United States Patent
Koguchi et al.

(10) Patent No.: US 6,800,742 B2
(45) Date of Patent: Oct. 5, 2004

(54) METHOD FOR PRODUCING β-D-RIBOFURANOSE DERIVATIVES OR OPTICAL ISOMERS THEREOF

(75) Inventors: Yoshihito Koguchi, Kawasaki (JP); Takayoshi Torii, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/100,909

(22) Filed: Mar. 20, 2002

(65) Prior Publication Data

US 2002/0187942 A1 Dec. 12, 2002

(30) Foreign Application Priority Data

May 22, 2001 (JP) ........................................ 2001-152336

(51) Int. Cl.$^7$ ........................ C07H 15/00; C07H 17/00; C07G 3/00
(52) U.S. Cl. .................... 536/18.6; 536/17.2; 536/17.4; 536/17.7; 536/18.1; 536/18.2; 536/18.5
(58) Field of Search ................................ 536/17.4, 4.1, 536/17.2, 17.7, 18.1, 18.2, 18.5, 18.6

(56) References Cited

FOREIGN PATENT DOCUMENTS

| WO | WO 95 02604 A |   | 1/1995 |
|----|---------------|---|--------|
| WO | WO 98/28319   | * | 7/1998 |

OTHER PUBLICATIONS

Schwögler et al. ("Synthesis and Properties of Flavin Ribofuranosides and Flavin Ribopyranosides", Helvetica Chimica Acta, vol. 83, pp. 2452–2463, 2000).*
R. K. Ness, et al., *J. Am. Chem. Soc*, vol. 76, pp. 763–767 (1954).
R. R. Schmidt, et al., *Liebigs Ann. Chem.*, pp. 1856–1863 (1974).
Mizutani, K. et al.: "N.M.R. Spectral Study of Alpha–and Beta–L–Arabinofuranosides", Carbohydrate Research, vol. 185, pp. 27–38 (1989).
Schmidt, Richard R. et al.: "Functional Riburonic Acid Derivatives", Chem. Ber. 111, pp. 3311–3324 (1978).

* cited by examiner

*Primary Examiner*—James O. Wilson
*Assistant Examiner*—Traviss C. McIntosh, III
(74) *Attorney, Agent, or Firm*—Oblon, Spivak, McClelland, Maier & Neustadt, P.C.

(57) ABSTRACT

The present invention provides a method for efficiently producing β-D-ribofuranose derivatives or optical isomers thereof, useful as synthetic intermediates of pharmaceutical nucleic acid-series products. The method comprises a step of producing 1-O-benzyl-β-D-ribofuranose-2,3,5-triacetate or an optical isomer thereof by allowing β-D-ribofuranose-1,2,3,5-tetraacetate or an optical isomer thereof to react with a benzyl alcohol in the presence of acid catalysts and a step of hydrolyzing the resulting 1-O-benzyl-β-D-ribofuranose-2,3,5-triacetate in the presence of a base to produce 1-O-benzyl-β-D-ribofuranose or an optical isomer thereof.

16 Claims, No Drawings

METHOD FOR PRODUCING β-D-RIBOFURANOSE DERIVATIVES OR OPTICAL ISOMERS THEREOF

CROSS REFERENCES TO RELATED APPLICATIONS

This application claims priority to Japanese Patent Application No. 152336/2001, filed May 22, 2001, and which is incorporated herein by reference in its entirely.

BACKGROUND OF THE INVENTION

1. Field of the Invention

The present invention relates to a method for producing certain β-D-ribofuranose derivatives (one of the structural components of certain nucleic acid compounds) or optical isomers thereof. More specifically, the invention relates to a method for producing β-D-ribofuranose derivatives represented by the following general formulas (1), (3), and (6) (including the β-L-ribofuranose derivatives as the optical isomers thereof) from the starting material β-D-ribofuranose-1,2,3,5-tetraacetate or an optical isomer thereof, and a method for producing a series of these synthetic intermediates.

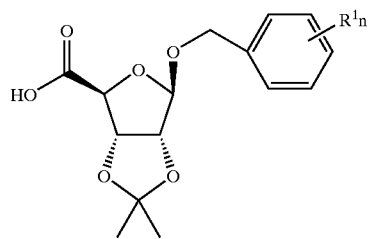
(1)

wherein $R^1$ represents a hydrogen atom or a substituent and n represents an integer of 1 to 5.

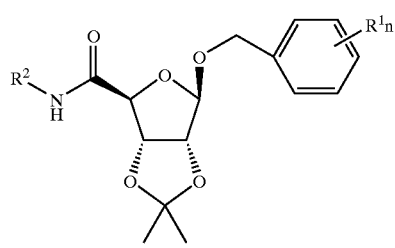
(3)

wherein $R^1$ and n have the same meanings as described above and $R^2$ represents a hydrogen atom or an alkyl group with 1 to 6 carbon atoms.

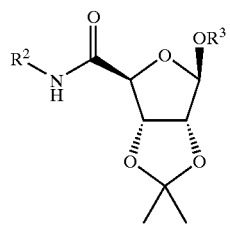
(6)

wherein $R^2$ has the same meaning as described above, and $R^3$ represents an alkyl group with 1 to 6 carbon atoms.

2. Discussion of the Background

Compound A, shown below, may be prepared by substituting the hydroxyl group at the 5' position of the sugar moiety (β-D-ribofuranose) of a nucleic acid with a carboxylic acid amide as represented by the following formula (A), and has bee n recently reported in the forms of numerous pharmaceutical products of adenosine agonists, as described in U.S. Pat. No. 4,968,697 and the published International Patent Application Nos. WO 9502604, WO 9314102, WO 9518817, WO 9423723, and WO 9417090.

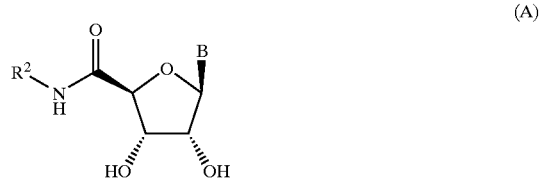
(A)

wherein B represents a nucleic acid base such as an adenine derivative; and $R^2$ represents a hydrogen or an alkyl group with 1 to 6 carbon atoms.

To date, Compound A has been synthetically prepared by the following synthesis scheme: (1) protecting the hydroxyl group at the 2'- and 3'-positions of the β-D-ribofuranose of a nucleic acid with isopropylidene and the like; (2) oxidizing the hydroxyl group at the 5'-position; (3) amidating the resulting carboxylic acid; and (4) subsequently eliminating the protective groups.

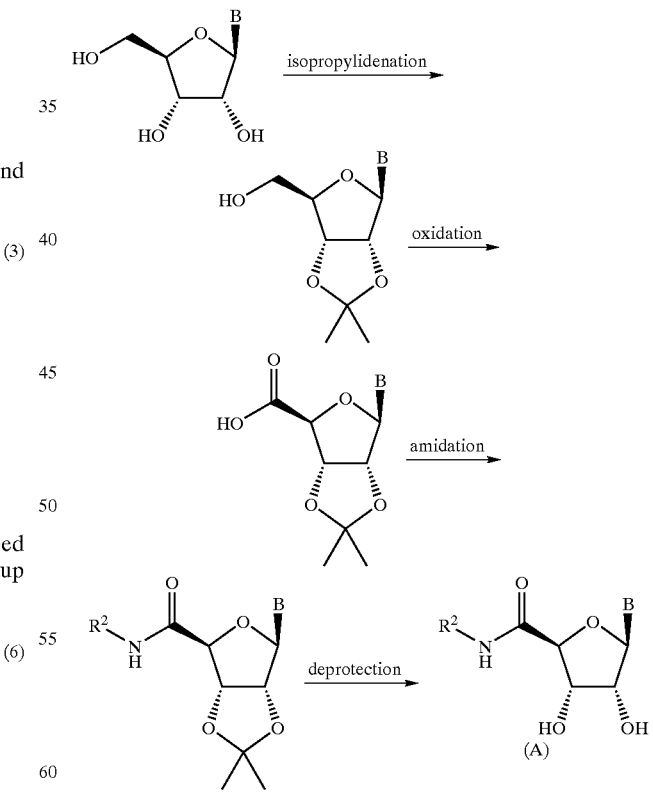

Meanwhile, the present inventors have focused their attention on the possibility that the compound represented by the general formula (A) may be synthetically prepared by coupling the nucleic acid base moiety B with β-D-ribofuranose derivative represented by the general formula (C), which is a route totally unlike the synthetic process described above. In this synthetic process, the sugar moiety, which is readily eliminated from the nucleic acid under acidic conditions, is introduced at the final stage. Thus, the nucleic acid base moiety can be synthetically prepared, separately, under various reaction conditions and attached to the sugar moiety after it has been prepared. Thus, the process is more convenient for the synthesis of compounds with various modified nucleic acid base moieties than the previous process is.

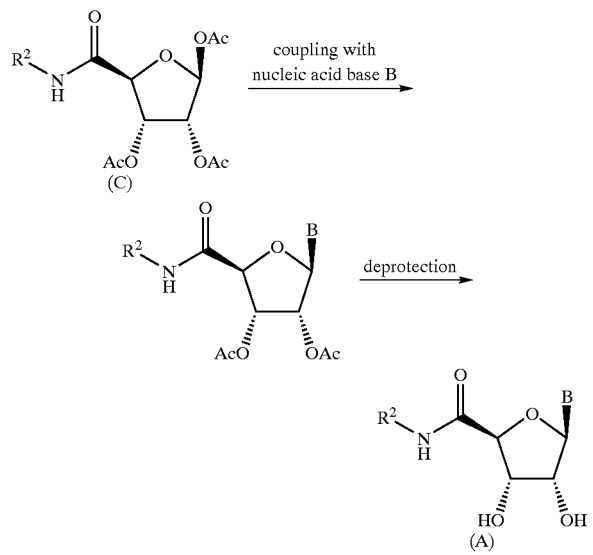

wherein Ac represents an acetyl group; and B and $R^2$ individually have the same meanings as described above.

It is suggested that the β-D-ribofuranose derivative represented by the general formula (C) can be readily prepared synthetically from the carboxylic acid compound with the structure of the general formula (1), by amidating of the carboxylic acid compound into amide compounds (3) and (6) and then triacetylating the amide compounds. Hence, the compounds of the structures of the general formulas (1), (3), and (6) may be important intermediates of pharmaceutical products containing a backbone of the general formula (A). Additionally, the optical isomers of these compounds will also be promising as pharmaceutical intermediates.

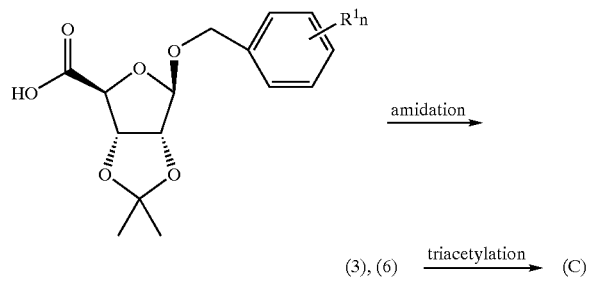

The compound of the structure of the general formula (6) has previously been prepared synthetically, as described mainly for compounds with a methoxy group at the 1-position in, for example, Liebigs Ann. Chem., 1974, 1856–63, by: (1) methylating the hydroxyl group at the 1-position in the starting material β-D-ribofuranose; (2) protecting the hydroxyl group at the 2- and 3-positions of the resulting 1-O-methoxy-β-D-ribofuranose with isopropylidene and the like; and then (3) oxidizing the hydroxyl group at the 5-position. The synthetic route is as follows.

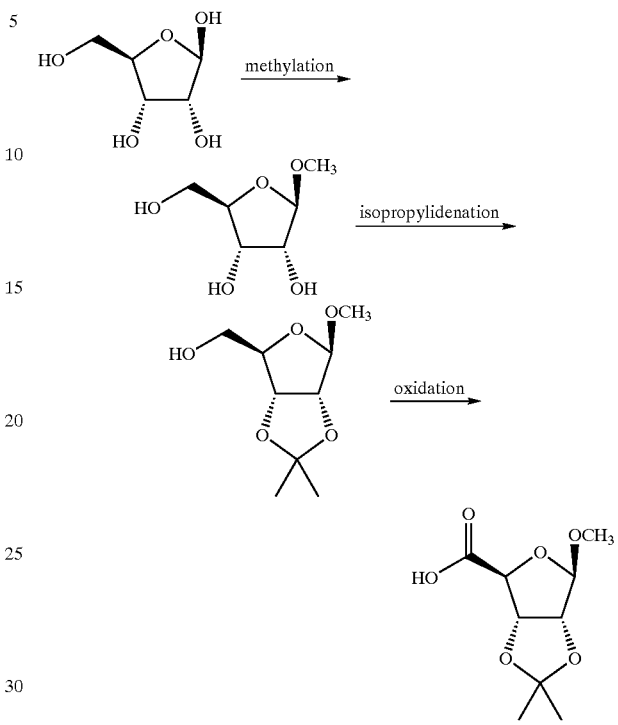

The known process however gives a low total yield from the raw material β-D-ribofuranose. Because both the α form and β form are essentially produced in the methylation of the hydroxyl group at the 1-position in β-D-ribofuranose in the presence of acid catalysts, the reduction of the yield is unavoidable and the purification is difficult. The benzylation of the hydroxyl group at the 1-position in β-D-ribofuranose also has a yield as low as 38% (see J. Am. Chem. Soc., vol. 76, pp. 763–767 (1954)). Accordingly, no reaction has been known for introducing alkoxyl group into the 1-position of the β-D-ribofuranose backbone at a high yield and in a highly β-selective manner.

Additionally, the oxidation of a compound prepared by substituting the hydroxyl group at the 2- and 3-positions in 1-O-methoxy-β-D-ribofuranose with isopropylidene is essential for the synthesis of a carboxylic acid compound of the structure of the general formula (3). For the compound with a methoxy group at 1-position, oxidation using potassium permanganate (Liebigs Ann. Chem., 1974, 1856–63) and oxidation using 2,2,6,6-tetramethylpiperidinyl-1-oxy (TEMPO) (WO 9828319) have been known. However, in these oxidations, the raw materials are so syrupy that the raw materials are purified with much difficulty. The oxidations have been problematic in terms of high reproducibility, since many examples have been known of the blocking of the progress of the oxidation reactions in the presence of even a trace amount of impurities.

SUMMARY OF THE INVENTION

Accordingly, it is one object of the present invention to provide novel methods for producing the compounds of the general formulas (1), (3), and (6) or optical isomers thereof in high yields.

It is another object of the present invention to provide novel methods for producing a series of intermediates, which are useful for producing the compounds of the general formulas (1), (3), and (6) or optical isomers thereof, in high yields.

These and other objects, which will become apparent during the course of the following detailed description, have been achieved by the inventors' surprising discovery that 1-O-benzyl-β-D-ribofuranose-2,3,5-triacetate can be produced with high efficiency, by preliminarily acetylating the hydroxyl groups at the 1-, 2-, 3, and 5-positions of β-D-ribofuranose to afford β-D-ribofuranose-1,2,3,5-tetracetate, and then allowing the resulting tetraacetate form to react with a benzyl alcohol in the presence of an acid to benzylate the 1-position of the ribofuranose backbone in high yield and in a highly β-selective manner. Additionally, the inventors have found a method for synthetically preparing 1-O-benzyl-β-D-ribofuranose in high yield by subsequently hydrolyzing the resulting benzyl compound.

The inventors have also found that, because not only 1-O-benzyl-β-D-ribofuranose but also a compound prepared by protecting the hydroxyl groups at the 2- and 3-positions in the ribofuranose with isopropylidene group can be recovered as crystals, the purification thereof can be readily achieved, and that the control of the TEMPO oxidation of the raw material 1-O-benzyl-2,3-isopropylidene-β-D-ribofuranose detectable via ultraviolet absorption by HPLC analysis can be carried out readily and the reaction progresses at a high yield.

Based on these two key reactions, the inventors have successfully synthetically prepared the compounds represented by the general formulas (1), (3), and (6) from the raw material β-D-ribofuranose-1,2,3,5-tetraacetate in high yields. Thus, the invention has been achieved. The present methods can be used for the production of optical isomers of these compounds.

More specifically, the invention in a first aspect provides a method for producing 1-O-benzyl-β-D-ribofuranose-2,3,5-triacetate optionally having one or more substituents on the benzene ring or an optical isomer thereof, comprising:
    reacting β-D-ribofuranose-1,2,3,5-tetraacetate or an optical isomer thereof with a benzyl alcohol optionally having one or more substituents on the benzene ring in the presence of an acid catalyst, to obtain said 1-O-benzyl-β-D-ribofuranose-2,3,5-triacetate optionally having one or more substituents on the benzene ring or an optical isomer thereof.

In a second aspect, the present invention provides a method for producing 1-O-benzyl-β-D-ribofuranose optionally having one or more substituents on the benzene ring or an optical isomer thereof, comprising:
    hydrolyzing the 1-O-benzyl-β-D-ribofuranose-2,3,5-triacetate optionally having one or more substituents on the benzene ring or an optical isomer thereof prepared by a method according to the first aspect, to obtain said 1-O-benzyl-β-D-ribofuranose optionally having one or more substituents on the benzene ring or an optical isomer thereof.

In a third aspect, the present invention provides a method for producing 1-O-benzyl-2,3-isopropylidene-β-D-ribofuranose optionally having one or more substituents on the benzene ring or an optical isomer thereof, comprising:
    reacting the 1-O-benzyl-β-D-ribofuranose optionally having one or more substituents on the benzene ring or an optical isomer thereof prepared by a method according to the second aspect with 2,2-dimethoxypropane or acetone in the presence of an acid catalyst, to obtain said 1-O-benzyl-2,3-isopropylidene-β-D-ribofuranose optionally having one or more substituents on the benzene ring or an optical isomer thereof.

In a fourth aspect, the present invention provides a method for producing an (3aS, 4S, 6R, 6aR)-6-benzyloxy-2,2-dimethyltetrahydro-furo[3,4-d][1,3]dioxole-4-carboxylic acid optionally having one or more substituents on the benzene ring, as represented by the general formula (1):

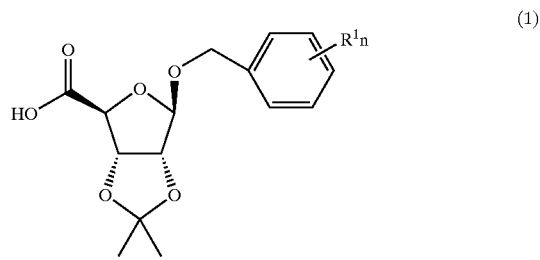

wherein $R^1$ represents hydrogen atom or a substituent; and n represents an integer of 1 to 5, or an optical isomer thereof, comprising:
    oxidizing the 1-O-benzyl-2,3-isopropylidene-β-D-ribofuranose optionally having one or more substituents on the benzene ring or an optical isomer thereof prepared by a method according to the third aspect with 2,2,6,6-tetramethylpiperidinyl-1-oxy, to obtain said (3aS, 4S, 6R, 6aR)-6-benzyloxy-2,2-dimethyltetrahydro-furo[3,4-d][1,3]dioxole-4-carboxylic acid optionally having one or more substituents on the benzene ring.

In a fifth aspect, the present invention provides a method for producing an (3aS, 4S, 6R, 6aR)-6-benzyloxy-2,2-dimethyltetrahydro-furo[3,4-d][1,3]dioxole-4-carboxylic acid amide derivative optionally having one or more substituents on the benzene ring, as represented by the general formula (3):

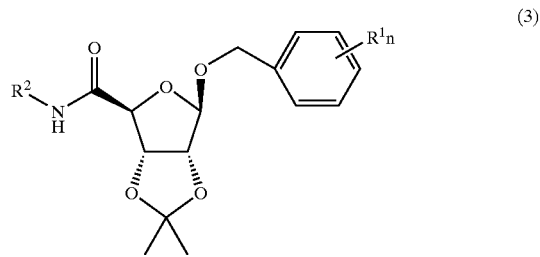

wherein $R^1$ represents hydrogen atom or a substituent; n represents an integer of 1 to 5; and $R^2$ represents hydrogen or an alkyl group with 1 to 6 carbon atoms, or an optical isomer thereof, comprising:
    reacting the (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof prepared by a method according to the fourth aspect with thionyl chloride, to obtain a reaction product; and
    reacting said reaction product with an amine represented by the general formula (2):

wherein $R^2$ has the same meaning as described above, to obtain said (3aS, 4S, 6R, 6aR)-6-benzyloxy-2,2- dimethyltetrahydro-furo[3,4-d][1,3]dioxole-4-carboxylic acid amide derivative optionally having one or more substituents on the benzene ring.

In a sixth aspect, the present invention provides a method for producing an (3aS, 4S, 6R, 6aR)-6-alkoxy-2,2-dimethyltetrahydro-furo[3,4-d][1,3]dioxole-4-carboxylic acid amide derivative optionally having one or more substituents on the benzene ring, as represented by the general formula (6):

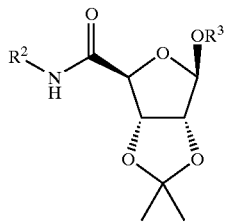

(6)

wherein $R^2$ represents hydrogen or an alkyl group with 1 to 6 carbon atoms, and $R^3$ represents an alkyl group with 1 to 6 carbon atoms, or an optical isomer thereof, comprising:

reacting the (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof prepared by a method according to the fourth aspect with an aliphatic alcohol represented by the general formula (4):

$$R^3\text{—OH} \tag{4}$$

wherein $R^3$ has the same meaning as described above, in the presence of an acid catalyst, to obtain a reaction product; and then continuously reacting said reaction product with 2,2-dimethoxypropane or acetone in the presence of an acid catalyst to obtain a compound represented by the general formula (5):

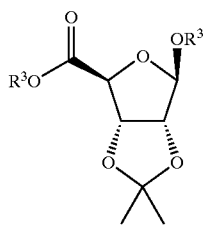

(5)

wherein $R^3$ has the same meaning as described above, or an optical isomer thereof, subsequently reacting said compound of formula (5) with an amine represented by the general formula (2):

$$R^2\text{—NH}_2 \tag{2}$$

wherein $R^2$ has the same meaning as described above, to obtain said (3aS, 4S, 6R, 6aR)-6-alkoxy-2,2-dimethyltetrahydro-furo[3,4-d][1,3]dioxole-4-carboxylic acid amide derivative optionally having one or more substituents on the benzene ring.

In a seventh aspect, the present invention provides a method for producing an (3aS, 4S, 6R, 6aR)-6-benzyloxy-2,2-dimethyltetrahydro-furo[3,4-d][1,3]dioxole-4-carboxylic acid optionally having one or more substituents on the benzene ring, as represented by the general formula (1):

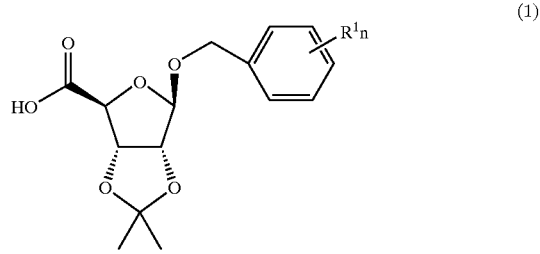

(1)

wherein $R^1$ represents hydrogen atom or a substituent; and n represents an integer of 1 to 5, or an optical isomer thereof, comprising:

oxidizing 1-O-benzyl-2,3-isopropylidene-β-D-ribofuranose optionally having one or more substituents on the benzene ring or an optical isomer thereof with 2,2,6,6-tetramethyl-piperidinyl-1-oxy, to obtain said (3aS, 4S, 6R, 6aR)-6-benzyloxy-2,2-dimethyltetrahydro-furo[3,4-d][1,3]dioxole-4-carboxylic acid optionally having one or more substituents on the benzene ring.

In an eighth aspect, the present invention provides a method for producing an (3aS, 4S, 6R, 6aR)-6-benzyloxy-2,2-dimethyltetrahydro-furo[3,4-d][1,3]dioxole-4-carboxylic acid amide derivative optionally having one or more substituents on the benzene ring as represented by the general formula (3):

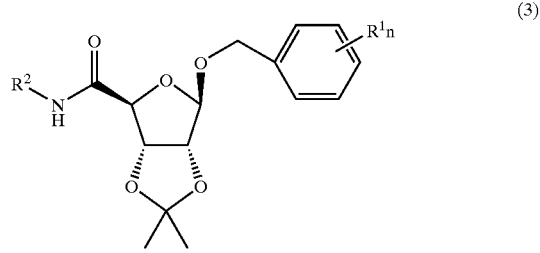

(3)

wherein $R^1$ represents hydrogen atom or a substituent; n represents an integer of 1 to 5; and $R^2$ represents hydrogen or an alkyl group with 1 to 6 carbon atoms, or an optical isomer thereof, comprising:

reacting the (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof prepared by a method according to the seventh aspect with thionyl chloride, to obtain a reaction product; and reacting said reaction product with an amine represented by the general formula (2):

$$R^2\text{—NH}_2 \tag{2}$$

wherein $R^2$ has the same meaning as described above, to obtain said (3aS, 4S, 6R, 6aR)-6-benzyloxy-2,2-dimethyltetrahydro-furo[3,4-d][1,3]dioxole-4-carboxylic acid amide derivative optionally having one or more substituents on the benzene ring.

In a ninth aspect, the present invention provides a method for producing (3aS, 4S, 6R, 6aR)-6-alkoxy-2,2-dimethyltetrahydro-furo[3,4-d][1,3]dioxole-4-carboxylic acid amide derivative represented by the general formula (6):

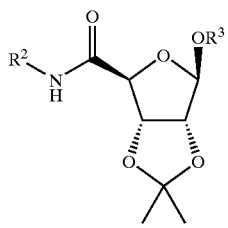

wherein R² represents hydrogen or an alkyl group with 1 to 6 carbon atoms and R³ represents an alkyl group with 1 to 6 carbon atoms, or an optical isomer thereof or an optical isomer thereof, comprising reacting the (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof prepared by a method according to the seventh aspect with an aliphatic alcohol represented by the general formula (4):

$$R^3\text{—OH} \quad (4)$$

wherein R³ has the same meaning as described above, in the presence of an acid catalyst, to obtain a reaction product; and reacting said reaction product with 2,2-dimethoxypropane or acetone in the presence of an acid catalyst to prepare a compound represented by the general formula (5):

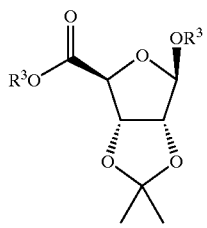

wherein R³ has the same meaning as described above, or an optical isomer thereof; and reacting said compound of formula (5) or an optical isomer thereof with an amine represented by the general formula (2):

$$R^2\text{—NH}_2 \quad (2)$$

wherein R² has the same meaning as described above, to obtain said (3aS, 4S, 6R, 6aR)-6-alkoxy-2,2-dimethyltetrahydro-furo[3,4-d][1,3]dioxole-4-carboxylic acid amide derivative.

DETAILED DESCRIPTION OF THE PREFERRED EMBODIMENTS

In accordance with the present invention, the β-ribofuranose-1,2,3,5-tetracetate includes both β-D-ribofuranose-1,2,3,5-tetraacetate and β-L-ribofuranose-1,2,3,5-tetraacetate. Hereinbelow, the process is mainly described in the context of using β-D-ribofuranose-1,2,3,5-tetraacetate as an example. However, it is to be understood that the following is also absolutely correct for the process using β-L-ribofuranose-1,2,3,5-tetraacetate or for the production of racemic mixtures or mixtures containing any degree of enantiomeric excess of either the D or L enantiomer.

The production process flow of the β-D-ribofuranose derivatives represented by the general formulas (1), (3), and (6) from the raw material β-D-ribofuranose-1,2,3,5-tetraacetate in accordance with the present invention is illustrated in the chemical reaction scheme shown below.

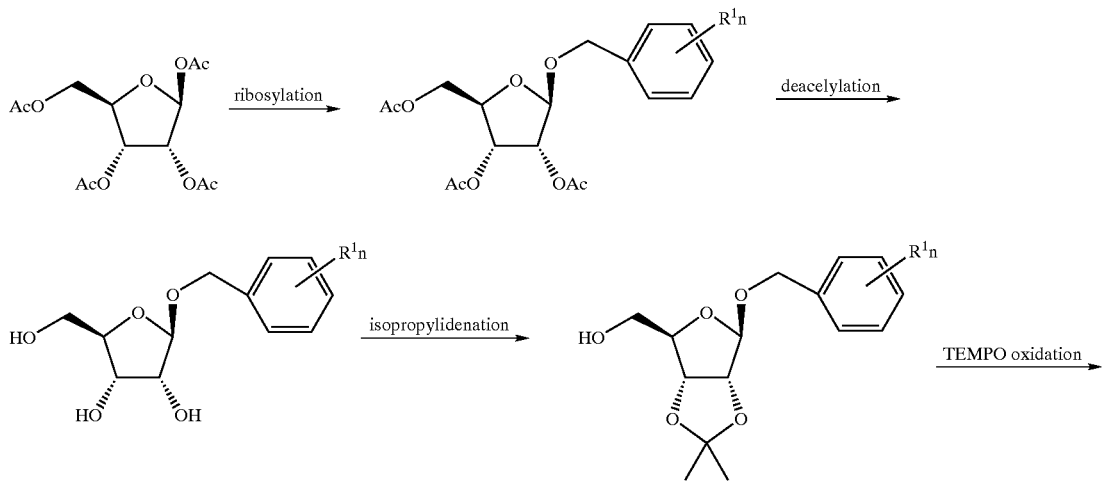

-continued

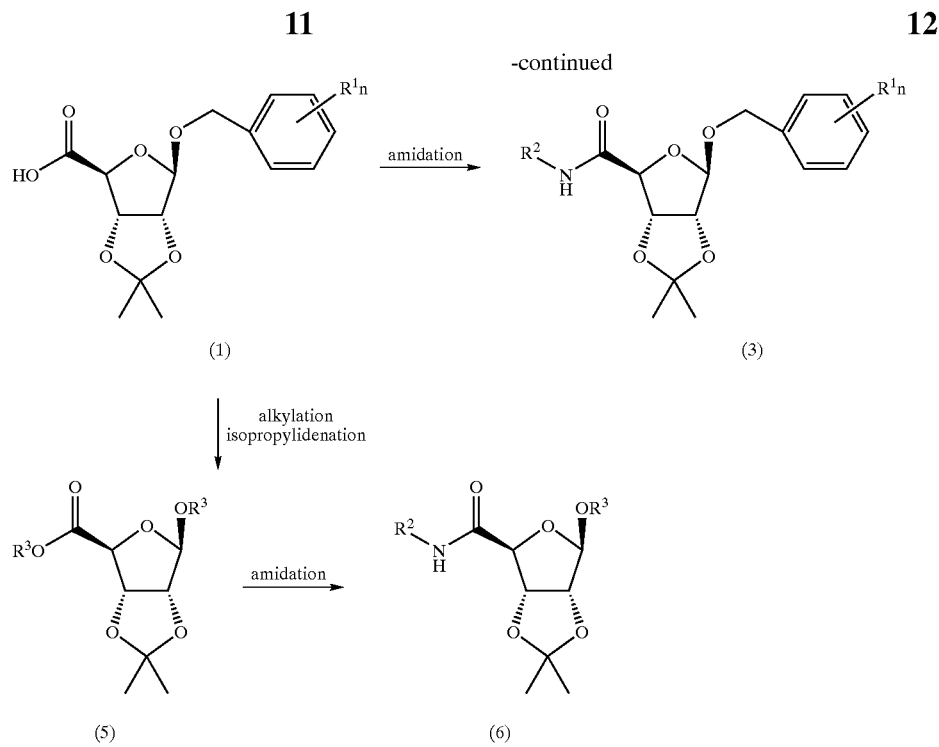

The steps of the production process are now sequentially described below. (1) First, the ribosylation (1-benzyloxylation) reaction of β-D-ribofuranose-1,2,3,5-tetraacetate (or β-L-ribofuranose-1,2,3,5-tetraacetate) with benzyl alcohol optionally having one or more substituents on the benzene ring is conducted in the presence of an acid catalyst in a non-protonic organic solvent. For the benzyl alcohol optionally having one or more substituents on the benzene ring thereof, the substituents may include, for example, an alkyl group with 1 to 6 carbon atoms, an alkoxyl group with 1 to 6 carbon atoms, a nitro group, halogen atoms (chlorine, bromine, iodine and the like), an alkoxycarbonyl group with 1 to 7 carbon atoms, a cyano group, and a hydroxyl group. Such benzyl alcohols optionally having one or more substituents on the benzene ring may be used at an amount of 1 to 10 equivalents, preferably 1 to 2 equivalents, to (per) 1 equivalent of the raw material β-D-ribofuranose-1,2,3,5-tetraacetate (or β-L-ribofuranose-1,2,3,5-tetraacetate). Further, the acid catalyst may be, for example, a Lewis acid (for example, zinc bromide, zinc chloride, and aluminum chloride), an inorganic acid (for example, hydrochloric acid, sulfuric acid, and phosphoric acid) or an organic acid (for example, acetic acid, p-toluenesulfonic acid, and methanesulfonic acid). The acid catalyst is used at an amount of 0.5 to 4 equivalents, preferably 1 to 2 equivalents, to 1 equivalent of the raw material β-D-ribofuranose-1,2,3,5-tetraacetate (or β-L-ribofuranose-1,2, 3,5-tetraacetate).

The non-protonic organic solvent may be, for example, an aromatic hydrocarbon such as benzene, toluene, and xylene; a halogenated hydrocarbon such as chloroform and carbon tetrachloride; a ketone such as acetone and methyl ethyl ketone; an ester such as ethyl acetate; N,N-dimethylformamide; or dimethyl sulfoxide.

The reaction temperature is not necessarily fixed and depends on the alcohol type, the solvent type, and other conditions. Generally, the reaction temperature is ambient temperature (20° C.) to 150° C., preferably ambient temperature to 80° C. The reaction time varies, depending on the reaction temperature, so it is not defined precisely. However, generally, the reaction time is 1 to 24 hours, preferably 2 to 14 hours.

To isolate 1-O-benzyl-β-D-ribofuranose-2,3,5-triacetate optionally having one or more substituents on the benzene ring (or 1-O-benzyl-β-L-ribofuranose-2,3,5-triacetate) from the reaction mixture thus prepared, first, an aqueous layer is separated by adding saturated aqueous sodium hydrogen carbonate solution to the reaction mixture; organic solvents such as toluene are then used for extraction; and then, the resulting extract is washed with saturated aqueous sodium chloride solution, followed by distillation under reduced pressure; the resulting syrup may be purified, if necessary, by silica gel column chromatography, to recover 1-O-benzyl-β-D-ribofuranose-2,3,5-triacetate (or 1-O-benzyl-β-L-ribofuranose-2,3,5-triacetate) as crystals. The product can also be identified, as such, by further deacetylation thereof to give 1-O-benzyl-β-D-ribofuranose (or 1-O-benzyl-β-L-ribofuranose) quantitatively.

(2) The deacetylation (hydrolysis) of 1-O-benzyl-β-D-ribofuranose-2,3,5-triacetate (or 1-O-benzyl-β-L-ribofuranose-2,3,5-triacetate) optionally having one or more substituents on the benzene ring thereof is not particularly difficult. The deacetylation is promoted by adding a base or potassium cyanide at 0.01 to 3 equivalents, preferably 0.1 to 1 equivalent, to 1 equivalent of the triacetate in the presence of a lower alcohol solvent, for example methanol. As the base, use may be made of an organic base such as sodium methoxide, sodium ethoxide, pyridine and triethylamine; or an inorganic base such as sodium hydroxide, potassium hydroxide, sodium carbonate, potassium carbonate, sodium hydrogen carbonate, ammonia, and the like.

The reaction temperature is generally ambient temperature to 100° C., preferably ambient temperature to 50° C. The reaction time varies, depending on the reaction temperature, so it is not defined precisely. Generally, however, the reaction time is 0.5 to 24 hours, preferably 1 to 4 hours.

The reaction mixture thus recovered is distilled under reduced pressure, and the resulting oil is purified by silica gel column chromatography, if necessary, to recover crystals of 1-O-benzyl-β-D-ribofuranose (or 1-O-benzyl-β-L-ribofuranose).

(3) The isopropylidenation of 1-O-benzyl-β-D-ribofuranose (or 1-O-benzyl-β-L-ribofuranose) optionally having one or more substituents on the benzene ring is conducted, by adding an acid catalyst such as an inorganic acid (such as hydrochloric acid or sulfuric acid) or an organic acid (such as methanesulfonic acid or p-toluenesulfonic acid) at 0.01 to 1 equivalent, preferably 0.01 to 0.2 equivalent, along with 2,2-dimethoxypropane at 1 to 10 equivalents, preferably 1 to 2 equivalents, to 1 equivalent of the 1-O-benzyl-β-D-ribofuranose (or 1-O-benzyl-β-L-ribofuranose), in a non-protonic organic solvent, or in acetone used as the solvent.

The reaction temperature generally is ambient temperature to 100° C., preferably ambient temperature to 50° C. The reaction time varies, depending on the reaction temperature, so it is not defined precisely. However, generally, the reaction time is 0.5 to 24 hours, preferably 1 to 4 hours.

To the resulting reaction mixture may be added aqueous sodium hydrogen carbonate solution to separate an organic layer, which is concentrated under reduced pressure, to recover 1-O-benzyl-2,3-isopropylidene-β-D-ribofuranose (or 1-O-benzyl-2,3-isopropylidene-β-L-ribofuranose) as white crystals. The white crystals may be rinsed with a hexane/ethyl acetate mixture solvent in slurry to high purity.

(4) The TEMPO oxidation of 1-O-benzyl-2,3-isopropylidene-β-D-ribofuranose (or 1-O-benzyl-2,3-isopropylidene-β-L-ribofuranose) optionally having one or more substituents on the benzene ring is conducted in an aqueous basic solution such as aqueous sodium hydrogen carbonate solution, aqueous sodium carbonate solution, and aqueous potassium carbonate solution or a mixed solvent of such an aqueous basic solution with a non-protonic organic solvent. Using 2 to 20 equivalents (preferably 2 to 8 equivalents) of aqueous 10 to 15% sodium hypochlorite solution, 0.0001 to 0.1 equivalent (preferably 0.001 to 0.01 equivalent) of TEMPO (2,2,6,6-tetramethyl piperidinyl-1-oxy), and 0.05 to 1 equivalent (preferably 0.1 to 0.5 equivalent) of potassium bromide to 1 equivalent of the 1-O-benzyl-2,3-isopropylidene-β-D-ribofuranose (or 1-O-benzyl-2,3-isopropylidene-β-L-ribofuranose), the reaction may be carried out by charging the reactants and the solvents except for the aqueous sodium hypochlorite solution, and then dropwise adding the aqueous sodium hypochlorite solution while adjusting the inner temperature to 10° C. or less and adjusting the pH to 12 or more. After completion of the dropwise addition, the reaction temperature is maintained to 0° C. to 40° C., preferably 0° C. to ambient temperature. The reaction time is one to 5 hours, preferably 1 to 2 hours.

To separate and purify (3aS, 4S, 6R, 6aR)-6-benzyloxy-2,2-dimethyltetrahydro-furo[3,4-d][1,3]dioxole-4-carboxylic acid or an optical isomer thereof produced from the reaction mixture, for example, an organic layer may be separated by adding aqueous 10% sodium sulfite solution to the reaction mixture, to which is then added aqueous 7% sodium hydrogen carbonate solution, for reverse extraction; the resulting aqueous layer is adjusted to pH 2, using dilute hydrochloric acid, followed by extraction with an organic solvent such as ethyl acetate and distillation of the organic layer under reduced pressure, to recover the (3aS, 4S, 6R, 6aR)-6-benzyloxy-2,2-dimethyltetrahydro-furo[3,4-d][1,3]dioxole-4-carboxylic acid or an optical isomer thereof as crystals of high purity.

(5) The amidation of (3aS, 4S, 6R, 6aR)-6-benzyloxy-2,2-dimethyltetrahydro-furo[3,4-d][1,3]dioxole-4-carboxylic acid optionally having one or more substituents on the benzene ring thereof or an optical isomer thereof with ammonia or an alkylamine with 1 to 6 carbon atoms may be carried out by adding 1 to 3 equivalents, preferably 1 to 1.5 equivalents, of thionyl chloride to 1 equivalent of the carboxylic acid in a non-protonic organic solvent to convert the carboxylic acid into a carboxyl chloride. The reaction in this case is satisfactorily effected at ambient temperature to 100° C., preferably 40 to 70° C. for 1 hour to 5 hours, preferably 1 hour to 2 hours. Then, ammonia gas is continuously purged therein until the inner temperature reaches 55° C. The organic layer, separated by water addition to the reaction mixture, is concentrated under reduced pressure, to recover white crystals, which are then rinsed in hexane/ethyl acetate to recover (3aS, 4S, 6R, 6aR)-6-benzyloxy-2,2-dimethyl-tetrahydro-furo[3,4-d][1,3]dioxole-4-carboxylic acid amide or an optical isomer thereof as crystals. When an alkyl amine with 1 to 6 carbon atoms, for example methylamine, ethylamine, n-propylamine, butylamine, or hexylamine, is used instead of ammonia gas, the amidation is attained by adding the alkyl amine at 1 to 10 equivalents, preferably 1 to 3 equivalents, to 1 equivalent of the carboxylic acid, while the temperature is maintained at ambient temperature to 100° C., preferably 40 to 70° C.

(6) Alkylation, isopropylidenation, and amidation of (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof.

Using an aliphatic alcohol with 1 to 6 carbon atoms (for example, methanol, ethanol, n-propanol, amyl alcohol, and n-hexanol) as the solvent for the amidation, first, an inorganic acid or organic acid is added at 0.001 to 0.5 equivalent, preferably 0.01 to 0.1 equivalent, to 1 equivalent of the carboxylic acid so as to promote the alkylation. The reaction temperature varies depending on the type of an aliphatic alcohol, but generally, the temperature is selected from the range of 40° C. to the boiling point of the aliphatic alcohol used. In case of methanol, the temperature is 40 to 70° C., preferably 50 to 60° C., while the reaction time is 10 to 48 hours, preferably 20 to 30 hours.

Because of a partial elimination of the protective groups at the 2- and 3-positions under the alkylation conditions, the reaction solution is concentrated under reduced pressure for the purpose of completing the elimination; and the resulting residue is isopropylidated, using 2,2-dimethoxypropane at 1 to 10 equivalents, preferably 1 to 2 equivalents, (to 1 equivalent of the carboxylic acid initially used) as a non-protonic organic solvent or using acetone as the solvent. Then, aqueous 28% ammonia at 1 to 20 equivalents, preferably 1 to 10 equivalents, or an alkyl amine with 1 to 6 carbon atoms at 1 to 10 equivalents, preferably 1 to 3 equivalents, is added to the resulting reaction mixture for amidation. The reaction temperature for both the isopropylidenation and amidation is ambient temperature to 70° C., preferably ambient temperature to 40° C., while the reaction time for the both is 1 to 24 hours, preferably 1 to 14 hours. The organic layer, separated by water addition to the reaction mixture, is concentrated under reduced pressure, to recover white crystals, which are then rinsed in hexane/ethyl acetate, to recover the desired (3aS, 4S, 6R, 6aR)-6-alkoxy-2,2-dimethyltetrahydro-furo[3,4-d][1,3]dioxole-4-carboxylic acid amide or an optical isomer thereof as crystals.

Other features of the invention will become apparent in the course of the following descriptions of exemplary embodiments which are given for illustration of the invention and are not intended to be limiting thereof.

EXAMPLES

Example 1

Benzyl alcohol (0.57 mL, 5.5 mmol) was added to a solution of β-D-ribofuranose-1,2,3,5-tetraacetate (1.59 g, 5 mmol) and zinc chloride (681.4 mg, 5 mmol) in ethyl acetate (8 mL), and the mixture was stirred with heating to 60° C. for 2 hours. After cooling the mixture to ambient temperature, water (2 mL) was added to the resulting solution, for layer separation. The resulting organic layer was washed twice with aqueous 7% sodium hydrogen carbonate solution (2 mL) and subsequently concentrated under reduced pressure. The resulting oil was purified by silica gel column chromatography, to recover the desired 1-O-benzyl-β-D-ribofuranose-2,3,5-triacetate (1.56 g; yield of 85.1%) as a colorless solid. Melting point: 65° C.

Example 2

Benzyl alcohol (2.07 mL, 20 mmol) was added to a solution of β-D-ribofuranose-1,2,3,5-tetraacetate (3.18 g, 10 mmol) and zinc bromide (2.25 g, 10 mmol) in toluene (31.8 mL), and the mixture was stirred at ambient temperature for 20 hours. To the resulting solution was added aqueous saturated sodium hydrogen carbonate solution (31.8 mL), for layer separation. To the resulting aqueous layer was added toluene (31.8 mL) for extraction. The resulting two organic layers were combined together, washed with aqueous saturated sodium chloride solution (10 mL), dried over anhydrous magnesium sulfate, and concentrated under reduced pressure. To the resulting oily 1-O-benzyl-β-D-ribofuranose-2,3,5-triacetate were added methanol (31.8 mL) and a solution of 28% sodium methoxide in methanol (0.2 mL, 1 mmol), the mixture was stirred at ambient temperature for 2 hours, and the resulting mixture was concentrated under reduced pressure. The resulting oily matter was purified by silica gel column chromatography, to recover the desired 1-O-benzyl-β-D-ribofuranose (2.24 g; yield of 93.2%) as a white solid. Melting point: 95° C.

Example 3

Benzyl alcohol (1.14 mL, 11 mmol) was added to a solution of β-D-ribofuranose-1,2,3,5-tetraacetate (3.18 g, 10 mmol) and zinc chloride (1.36 g, 10 mmol) in ethyl acetate (16 mL), and the mixture was stirred at 60° C. for 2 hours. After cooling the reaction mixture to ambient temperature, water (4 mL) was added to the resulting solution, for layer separation, and the resulting organic layer was washed twice with aqueous 7% sodium hydrogen carbonate solution (4 mL), and concentrated under reduced pressure. To the resulting oily 1-O-benzyl-β-D-ribofuranose-2,3,5-triacetate were added methanol (16 mL) and a solution of 28% sodium methoxide in methanol (0.3 mL, 1.5 mmol), and the mixture was stirred at ambient temperature for 2 hours. The resulting organic layer was concentrated under reduced pressure. To the resulting oily 1-O-benzyl-β-D-ribofuranose were added ethyl acetate (16 mL), 2,2-dimethoxypropane (1.48 mL, 12 mmol) and methanesulfonic acid (0.13 mL, 2.0 mmol), and the mixture was stirred at ambient temperature for 15 hours. To the solution was added aqueous 7% sodium hydrogen carbonate solution (4 mL), for layer separation, and the resulting organic layer was concentrated under reduced pressure. To the resulting white solid was added a hexane/ethyl acetate (5:1) solution (6 mL) for rinsing as a slurry at ambient temperature for 2 hours. Subsequently, the solid was filtered and rinsed with a hexane/ethyl acetate (5:1) solution (1 mL). The solid was dried under reduced pressure to recover 1-O-benzyl-2,3-isopropylidene-β-D-ribofuranose (2.43 g; yield of 86.7%) as a white solid. Melting point: 108° C.

Example 4

To a solution of 1-O-benzyl-2,3-isopropylidene-β-D-ribofuranose (44.9 g, 160 mmol) in ethyl acetate (225 mL) were added aqueous 7% sodium hydrogen carbonate solution (240 mL), sodium hydrogen carbonate (11.7 g, 140 mmol), potassium bromide (2.87 g, 24 mmol) and 2,2,6,6-tetramethyl-1-piperidinyloxy (0.1 g, 0.64 mmol), and the resulting mixture was cooled to 0° C. To the solution was dropwise added aqueous 12% sodium hypochlorite solution (450 mL), while adjusting the inner temperature to 5° C. or less. After the dropwise addition, the temperature of the reaction solution was raised to ambient temperature and stirred for 30 minutes. To the solution was added aqueous 10% sodium sulfite solution (120 mL) for layer separation, and to the resulting organic layer was added aqueous 7% sodium hydrogen carbonate solution (80 mL) for reverse extraction. The resulting two aqueous layers were combined together, and the resulting solution was adjusted to pH 2, using an aqueous 6M hydrochloric acid solution, followed by extraction twice with ethyl acetate (230 mL). The resulting organic layer was concentrated under reduced pressure. The resulting solid was dried under reduced pressure, to recover (3aS, 4S, 6R, 6aR)-6-benzyloxy-2,2-dimethyltetrahydro-furo[3,4-d][1,3]dioxole-4-carboxylic acid (42.7 g; yield of 90.7%) as a white solid. Melting point: 79° C.

Example 5

To a solution of (3aS, 4S, 6R, 6aR)-6-benzyloxy-2,2-dimethyltetrahydro-furo[3,4-d][1,3]dioxole-4-carboxylic acid (35.3 g, 120 mmol) in ethyl acetate (350 mL) was added thionyl chloride (13.1 mL, 180 mmol), and the mixture was stirred with heating to 50° C. for one hour. After the solution was cooled to ambient temperature, ammonia gas was purged therein over 30 minutes. After cooling the solution to ambient temperature, water (120 mL) was added for layer separation, and the resulting organic layer was concentrated under reduced pressure. To the resulting solid was added a hexane/ethyl acetate (5:1) solution (200 mL) for rinsing as a slurry at ambient temperature for 14 hours. Subsequently, the solid was filtered and rinsed in a hexane/ethyl acetate (5:1) solution (20 mL). The solid was dried under reduced pressure to recover (3aS, 4S, 6R, 6aR)-6-benzyloxy-2,2-dimethyltetrahydro-furo[3,4-d][1,3]dioxole-4-carboxylic acid amide (29.8 g; yield of 84.3%) as a pale yellow solid. Melting point: 78° C.

Example 6

To a solution of (3aS, 4S, 6R, 6aR)-6-benzyloxy-2,2-dimethyltetrahydro-furo[3,4-d][1,3]dioxole-4-carboxylic acid (588.6 mg, 2 mmol) in methanol (8.8 mL) was added methanesulfonic acid (0.007 mL, 0.1 mmol), and the mixture was stirred with heating to 60° C. for 24 hours. After the solution was dried under reduced pressure, ethyl acetate (2.9 mL) and 2,2-dimethoxypropane (0.17 mL, 1.4 mmoL) were added to the resulting oil, and the mixture was stirring at ambient temperature for 2 hours. Aqueous 7% sodium hydrogen carbonate solution (0.5 mL) was added for layer separation, and the resulting organic layer was concentrated under reduced pressure, to which was added aqueous 28% ammonia (1.2 mL, 20 mmol), and the mixture was stirred at ambient temperature for 14 hours. To the resulting solution was added ethyl acetate (3 mL) for layer separation, and the organic layer was concentrated under reduced pressure. To the resulting solid was added a hexane/ethyl acetate (3:1) solution (3 mL) for rinsing as a slurry at ambient temperature for 2 hours. Subsequently, the solid was filtered and rinsed in a hexane/ethyl acetate (3:1) solution (0.5 mL). The solid was dried under reduced pressure to recover (3aS, 4S, 6R, 6aR)-6-methoxy-2,2-dimethyltetrahydro-furo[3,4-d][1,3]dioxol-4-carboxylic acid amide (278.7 mg; yield of 64.2%) as a white solid. Melting point: 136° C.

ADVANTAGES OF THE INVENTION

As described above, in accordance with the present invention, the reaction of β-D-ribofuranose-1,2,3,5-tetraacetate (β-L-ribofuranose-1,2,3,5-tetraacetate) with benzyl alcohols in the presence of acid catalyst can yield 1-O-benzyl-β-D-ribofuranose-2,3,5-triacetate (or 1-O-benzyl-β-L-ribofuranose-2,3,5-triacetate), in which the 1-position of the ribofuranose structure has been benzylated in a high yield and in a highly β-selective manner. Subsequent hydrolysis thereof can quantitatively convert the triacetate into 1-O-benzyl-β-D-ribofuranose (or 1-O-benzyl-β-L-ribofuranose). Because 1-O-benzyl-β-D-ribofuranose (or 1-O-benzyl-β-L-ribofuranose) and the compounds prepared by protecting the hydroxyl group at the 2- and 3-positions therein with isopropylidene group can be recovered as crystals, they can be readily purified. Additionally, the TEMPO oxidation of the raw material 1-O-benzyl-2,3-isopropylidene-β-D-ribofuranose (or 1-O-benzyl-2,3-isopropylidene-β-L-ribofuranose) detectable via ultraviolet absorption by HPLC analysis can be conducted under convenient control to a final high yield. The carboxylic acid generated via the oxidation can readily be converted further into carboxylic acid amide derivatives and the like, so the inventive methods are extremely meaningful as industrial processes of producing β-D-ribofuranose (or β-L-ribofuranose) derivatives useful as synthetic intermediates of pharmaceutical nucleic acid-series products.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A method for producing 1-O-benzyl-β-D-ribofuranose-2,3,5-triacetate optionally having one or more substituents on the benzene ring or an optical isomer thereof, comprising:
    reacting β-D-ribofuranose-1,2,3,5-tetraacetate or an optical isomer thereof with a benzyl alcohol optionally having one or more substituents on the benzene ring in the presence of an acid catalyst, to obtain said 1-O-benzyl-β-D-ribofuranose-2,3,5-triacetate optionally having one or more substituents on the benzene ring or optical isomer thereof,
    wherein said one or more substituents are selected from the group consisting of alkyl groups with 1 to 6 carbon atoms, alkoxyl groups with 1 to 6 carbon atoms, nitro groups, halogen atoms, alkoxycarbonyl groups with 1 to 7 carbon atoms, cyano groups, and hydroxyl groups.

2. A method for producing 1-O-benzyl-β-D-ribofuranose optionally having one or more substituents on the benzene ring or an optical isomer thereof, comprising:
    hydrolyzing 1-O-benzyl-β-D-ribofuranose-2,3,5-triacetate optionally having one or more substituents on the benzene ring or an optical isomer thereof, to obtain said 1-O-benzyl-β-D-ribofuranose optionally having one or more substituents on the benzene ring or an optical isomer thereof,
    wherein said 1-O-benzyl-β-D-ribofuranose-2,3,5-triacetate optionally having one or more substituents on the benzene ring or optical isomer thereof is prepared by the method of claim 1.

3. The method of claim 2, which comprises
    recovering 1-O-benzyl-β-D-ribofuranose-2,3,5-triacetate optionally having one or more substituents on the benzene ring or optical isomer thereof prior to hydrolyzing said 1-O-benzyl-β-D-ribofuranose-2,3,5-triacetate or optical isomer thereof.

4. A method for producing 1-O-benzyl-2,3-isopropylidene-β-D-ribofuranose optionally having one or more substituents on the benzene ring or an optical isomer thereof, comprising:
    reacting 1-O-benzyl-β-D-ribofuranose optionally having one or more substituents on the benzene ring or an optical isomer thereof with 2,2-dimethoxypropane or acetone in the presence of an acid catalyst, to obtain said 1-O-benzyl-2,3-isopropylidene-β-D-ribofuranose optionally having one or more substituents on the benzene ring or an optical isomer thereof,
    wherein said 1-O-benzyl-β-D-ribofuranose optionally having one or more substituents on the benzene ring or an optical isomer is prepared by the method of claim 2.

5. The method of claim 4, which comprises:
    recovering said 1-O-benzyl-β-D-ribofuranose optionally having one or more substituents on the benzene ring or an optical isomer thereof and allowing the resulting 1-O-benzyl-β-D-ribofuranose optionally having one or more substituents on the benzene ring or an optical isomer thereof to react with 2,2-dimethoxypropane or acetone in the presence of an acid catalyst.

6. A method for producing (3aS, 4S, 6R, 6aR)-6-benzyloxy-2,2-dimethyltetrahydro-furo[3,4-d][1,3]dioxole-4-carboxylic acid optionally having one or more substituents on the benzene ring, as represented by the general formula (1):

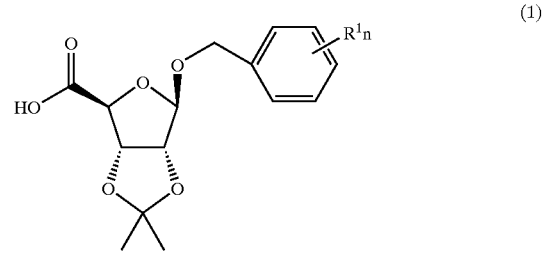

(1)

wherein $R^1$ represents a hydrogen atom or a substituent; and n represents an integer of 1 to 5, or an optical isomer thereof, and wherein said substituent is selected from the group consisting of alkyl groups with 1 to 6 carbon atoms, alkoxyl groups with 1 to 6 carbon atoms, nitro groups, halogen atoms, alkoxycarbonyl groups with 1 to 7 carbon atoms, cyano groups, and hydroxyl groups, comprising:
    oxidizing 1-O-benzyl-2,3-isopropylidene-β-D-ribofuranose optionally having one or more substituents on the benzene ring or an optical isomer thereof with 2,2,6,6-tetramethylpiperidinyl-1-oxy, to obtain said (3aS, 4S, 6R, 6aR)-6-benzyloxy-2,2-dimethyltetrahydro-furo[3,4-d][1,3]dioxole-4-carboxylic acid optionally having one or more substituents on the benzene ring, wherein said 1-O-benzyl-2,3-isopropylidene-β-D-ribofuranose optionally having one or more substituents on the benzene ring or an optical isomer thereof is prepared by the method of claim 4.

7. The method of claim 6, which comprises:
recovering 1-O-benzyl-2,3-isopropylidene-β-D-ribofuranose optionally having one or more substituents on the benzene ring or an optical isomer thereof, and oxidizing the resulting 1-O-benzyl-2,3-isopropylidene-β-D-ribofuranose optionally having one or more substituents on the benzene ring or an optical isomer thereof with 2,2,6,6-tetramethylpiperidinyl-1-oxy.

8. A method for producing (3aS, 4S, 6R, 6aR)-6-benzyloxy-2,2-dimethyltetrahydro-furo[3,4-d][1,3]dioxole-4-carboxylic acid amide derivative optionally having one or more substituents on the benzene ring, as represented by the general formula (3):

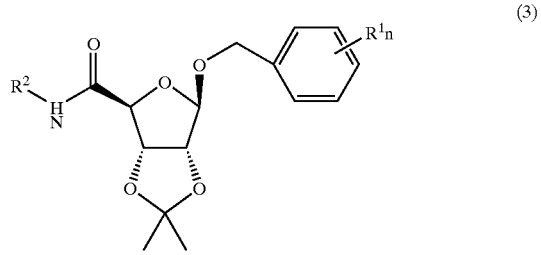

(3)

wherein R¹ represents hydrogen atom or a substituent; n represents an integer of 1 to 5, and wherein said substituent is selected from group consisting of alkyl group with 1 to 6 carbon atoms, alkoxyl groups with 1 to 6 carbon atoms, nitro groups, halogen atoms, alkoxycarbonyl groups with 1 to 7 carbon atoms, cyano groups, and hydroxyl groups; and R² represents hydrogen of an alkyl group with 1 to 6 carbon atoms, or an optical isomer thereof, comprising:

reacting (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof with thionyl chloride, to obtain a reaction product; and reacting said reaction product with an amine represented by the general formula (2):

R²—NH₂ (2)

wherein R² represents hydrogen or an alkyl group with 1 to 6 carbon atoms, to obtain said (3aS, 4S, 6R, 6aR)-6-benzyloxy-2,2-dimethyltetrahydro-furo[3,4-d][1,3]dioxole-4-carboxylic acid amide derivative optionally having one or more substituents on the benzene ring, wherein said (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof is prepared by the method of claim 6.

9. The method of claim 8, which comprises:
recovering (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof and allowing the resulting (3aS, 4S, 6R, 6aR)-6-benzyloxy-2,2-dimethyltetrahydro-furo[3,4-d][1,3]dioxole-4-carboxylic acid or an optical isomer thereof to react with thionyl chloride and then to react with an amine represented by the general formula (2):

R²—NH₂ (2)

wherein R² has the same meaning as described in claim 8.

10. A method for producing (3aS, 4S, 6R, 6aR)-6-alkoxy-2,2-dimethyltetrahydro-furo[3,4-d][1,3]dioxole-4-carboxylic acid amide derivative optionally having one or more substituents on the benzene ring, as represented by the general formula (6):

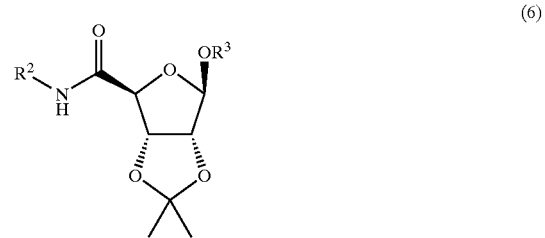

(6)

wherein R² represents hydrogen or an alkyl group with 1 to 6 carbon atoms and R³ represents an alkyl group with 1 to 6 carbon atoms or an optical isomer thereof, comprising:

reacting (3aS, 4S, 6R, 6aR)-6-benzyloxy-2,2-dimethyltetrahydro-furo [3,4-d][1,3]dioxole-4-carboxylic acid optionally having one or more substituents on the benzene ring or an optical isomer thereof with an aliphatic alcohol represented by the general formula (4):

R³—OH (4)

wherein R³ represents an alkyl group wit 1 to 6 carbon atoms, in the presence of an acid catalyst, to obtain a reaction product;

continuously reacting said reaction product with 2,2-dimethoxypropane or acetone in the presence of an acid catalyst, to obtain a compound represented by the general formula (5):

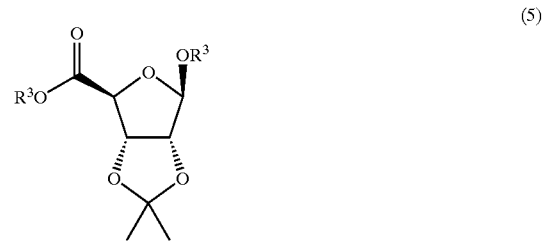

(5)

wherein R³ represents an alkyl group with 1 to 6 carbon atoms, or an optical isomer thereof; and subsequently reacting said compound of formula (5) with an amine represented by the general formula (2):

R²—NH₂ (2)

wherein R² represents hydrogen or an alkyl group with 1 to 6 carbon atoms, to obtain said (3aS, 4S, 6R, 6aR)-6-alkoxy-2,2-dimethyltetrahydro-furo[3,4-d][1,3 ]dioxole-4- carboxylic acid amide derivative optionally having one or more substituents on the benzene ring, wherein said (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof is prepared by the method of claim 6.

11. The method of claim 10, which comprises:

recovering said (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof and allowing the recovered (3aS, 4S, 6R, 6aR)-6-benzyloxy-2,2-dimethyltetrahydro-furo[3,4-d][1,3] dioxole-4-carboxylic acid or an optical isomer thereof to react with an aliphatic alcohol represented by the general formula (4):

$$R^3\text{—OH} \quad (4)$$

wherein $R^3$ represents an alkyl group with 1 to 6 carbon atoms, in the presence of an acid catalyst and then continuously to react with 2,2-dimethoxypropane or acetone in the presence of an acid catalyst to recover a compound represented by the general formula (5):

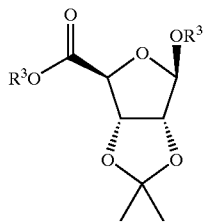

(5)

wherein $R^3$ represents an alkyl group with 1 to 6 carbon atoms, or an optical isomer thereof, which is subsequently allowed to react with an amine represented by the general formula (2):

$$R^2\text{—NH}_2 \quad (2)$$

wherein $R^2$ represents hydrogen or an alkyl group with 1 to 6 carbon atoms.

12. A method for producing (3aS, 4S, 6R, 6aR)-6-benzyloxy-2,2-dimethyltetrahydro-furo[3,4-d][(1,3] dioxole-4-carboxylic acid optionally having one or more substituents on the benzene ring, as represented by the general formula (1):

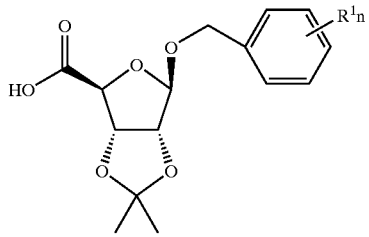

(1)

wherein $R^1$ represents hydrogen atom or a substituent; and n represents an integer of 1 to 5, or an optical isomer thereof, and wherein said substituent is selected from the group consisting of alkyl groups with 1 to 6 carbon atoms, alkoxyl groups with 1 to 6 carbon atoms, nitro groups, halogen atoms, alkoxycarbonyl groups with 1 to 7 carbon atoms, cyano groups, and hydroxyl groups, comprising:

oxidizing 1-O-benzyl-2,3-isopropylidene-β-D-ribofuranose optionally having one or more substituents on the benzene ring or an optical isomer thereof with 2,2,6,6-tetramethylpiperidinyl-1-oxy, to obtain said (3aS, 4S, 6R, 6aR)-6-benzyloxy-2,2-dimethyltetrahydro-furo[3,4-d][1,3]dioxole-4-carboxylic acid optionally having one or more substituents on the benzene ring, wherein said one or more substituents are selected from the group consisting of alkyl groups with 1 to 6 carbon atoms, alkoxyl groups with 1 to 6 carbon atoms, nitro groups, halogen atoms, alkoxycarbonyl groups with 1 to 7 carbon atoms, cyano groups, and hydroxyl groups.

13. A method for producing (3aS, 4S, 6R, 6aR)-6-benzyloxy-2,2-dimethyltetrahydro-furo[3,4-d][1,3]dioxol-4-carboxylic acid amide derivative optionally having one or more substituents on the benzene ring as represented by the general formula (3):

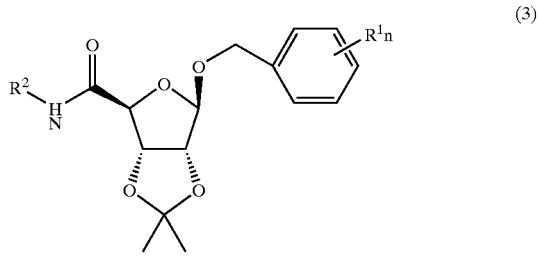

(3)

wherein $R^1$ represents a hydrogen atom or a substituent; n represents an integer of 1 to 5, and wherein said substituent is selected from the group consisting of alkyl groups with 1 to 6 carbon atoms, alkoxyl groups with 1 to 6 carbon atoms, nitro groups, halogen atoms, alkoxycarbonyl groups with 1 to 7 carbon atoms, cyano groups, and hydroxyl groups; and $R^2$ represents hydrogen or an alkyl group with 1 to 6 carbon atoms, or an optical isomer thereof, comprising:

reacting (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof with thionyl chloride, to obtain a reaction product; and reacting said reaction product with an amine represented by the general formula (2):

$$R^2\text{—NH}_2 \quad (2)$$

wherein $R^2$ represents hydrogen or an alkyl group with 1 to 6 carbon atoms, to obtain said (3aS, 4S, 6R, 6aR)-6-benzyloxy-2,2-dimethyltetrahydro-furo[3,4-d][1,3]dioxol-4-carboxylic acid amide derivative optionally having one or more substituents on the benzene ring, wherein said (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof is prepared by the method of claim 12.

14. The method of claim 13, which comprises:

recovering said (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof, and allowing the resulting (3aS, 4S, 6R, 6aR)-6-benzyloxy-2,2-dimethyltetrahydro-furo[3,4-d][1,3]

dioxole-4-carboxylic acid or an optical isomer thereof to react with thionyl chloride and then to react with an amine represented by the general formula (2):

  (2)

wherein R² represents hydrogen or an alkyl group with 1 to 6 carbon atoms.

15. A method for producing (3aS, 4S, 6R, 6aR)-6-alkoxy-2,2-dimethyltetrahydro-furo[3,4-d][1,3]dioxole-4-carboxylic acid amide derivative represented by the general formula (6):

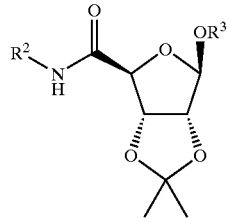  (6)

wherein R² represents a hydrogen or an alkyl group with 1 to 6 carbon atoms and R³ represents an alkyl group with 1 to 6 carbon atoms, or an optical isomer thereof, comprising:

reacting (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof with an aliphatic alcohol represented by the general formula (4):

R³—OH  (4)

wherein R³ represents an alkyl group with 1 to 6 carbon atoms, in the presence of an acid catalyst, to obtain a reaction product;

continuously reacting said reaction product with 2,2-dimethoxypropane or acetone in the presence of an acid catalyst, to obtain a compound represented by the general formula (5):

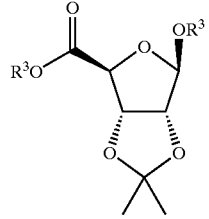  (5)

wherein R³ represents an alkyl group with 1 to 6 carbon atoms, or an optical isomer thereof; and reacting said compound of formula (5) with an amine represented by the general formula (2):

R²—NH₂  (2)

wherein R² represents hydrogen or an alkyl group with 1 to 6 carbon atoms, to obtain said (3aS, 4S, 6R, 6aR)-6-alkoxy-2,2-dimethyltetrahydro-furo[3,4-d][1,3]dioxole-4-carboxylic acid amide derivative, wherein said (3aS, 4S, 6R, 6aR)-6-benzyloxy-2,2-dimethyltetrahydro-furo[3,4-d][1,3]dioxole-4-carboxylic acid optionally having one or more substituents on the benzene ring or an optical isomer thereof is prepared by the method of claim 12.

16. The method of claim 15, which comprises:

recovering said (3aS, 4S, 6R, 6aR)-6-benzyloxy-2,2-dimethyltetrahydro-furo[3,4-d][1,3]dioxoe-4-carboxylic acid optionally having one or more substituents on the benzene ring or an optical isomer thereof, allowing the resulting (3aS, 4S, 6R, 6aR)-6-benzyloxy-2,2-dimethyltetrahydro-furo[3,4-d][1,3]dioxole-4-carboxylic acid or an optical isomer thereof to react with an aliphatic alcohol represented by the general formula (4):

R³—OH  (4)

wherein R³ represents an alkyl group with 1 to 6 carbon atoms, in the presence of an acid catalyst, and then continuously to react with 2,2-dimethoxypropane or acetone in the presence of an acid catalyst to prepare a compound represented by the general formula (5):

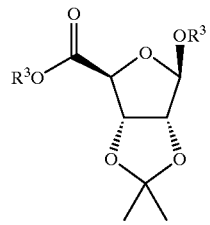  (5)

wherein R³ represents an alkyl group with 1 to 6 carbon atoms, or an optical isomer thereof, which is then allowed to react with an amine represented by the general formula (2):

R²—NH₂  (2)

wherein R² represents hydrogen or an alkyl group with 1 to 6 carbon atoms.

* * * * *